(12) United States Patent
Lund

(10) Patent No.: US 10,856,524 B2
(45) Date of Patent: Dec. 8, 2020

(54) SYSTEM AND METHOD FOR ANIMAL CORRALLING AND TRACKING

(71) Applicant: Steven J. Lund, Manti, UT (US)

(72) Inventor: Steven J. Lund, Manti, UT (US)

(73) Assignee: Steven J. Lund, Manti, UT (US)

( * ) Notice: Subject to any disclaimer, the term of this patent is extended or adjusted under 35 U.S.C. 154(b) by 111 days.

(21) Appl. No.: 16/036,927

(22) Filed: Jul. 16, 2018

(65) Prior Publication Data
US 2020/0015452 A1    Jan. 16, 2020

(51) Int. Cl.
| | |
|---|---|
| *A61B 5/00* | (2006.01) |
| *A01K 11/00* | (2006.01) |
| *A01K 15/02* | (2006.01) |
| *A61B 5/0205* | (2006.01) |
| *A61B 5/024* | (2006.01) |
| *A61B 5/08* | (2006.01) |
| *A61B 5/11* | (2006.01) |
| *A61B 5/145* | (2006.01) |

(52) U.S. Cl.
CPC .......... *A01K 11/008* (2013.01); *A01K 11/004* (2013.01); *A01K 15/028* (2013.01); *A61B 5/002* (2013.01); *A61B 5/02055* (2013.01); *A61B 5/6815* (2013.01); *A61B 5/02438* (2013.01); *A61B 5/0816* (2013.01); *A61B 5/1112* (2013.01); *A61B 5/14546* (2013.01); *A61B 2503/40* (2013.01)

(58) Field of Classification Search
CPC .... A01K 11/006; A01K 15/023; A01K 29/00; A01K 15/021; A01K 11/00; A01K 11/004; A01K 11/007; A01K 11/008; A01K 15/028; A01K 15/029; A01K 15/04; A01K 29/005; A61B 5/002; A61B 5/02055; A61B 5/6815
USPC ....... 119/720, 712, 721, 174, 421, 719, 905, 119/837; 340/573.3
See application file for complete search history.

(56) References Cited

U.S. PATENT DOCUMENTS

| | | | | |
|---|---|---|---|---|
| 4,262,632 | A | * | 4/1981 | Hanton .............. G06K 19/0723 119/51.02 |
| 4,510,495 | A | * | 4/1985 | Sigrimis .................. G07C 9/28 340/10.34 |

(Continued)

*Primary Examiner* — Yvonne R Abbott-Lewis
(74) *Attorney, Agent, or Firm* — Malone IP Law; Steven J. Malone

(57) ABSTRACT

A method of animal corralling and tracking includes: implanting an electronic device within an animal, the electronic device comprising one or more processors with non-transitory memory; receiving, with the electronic device, a GPS (global positioning satellite) signal defining a current location of the animal; selecting, on a digital map, acceptable GPS coordinate locations forming one or more geographic regions with one or more perimeter boundaries; wirelessly programming the electronic device with the selected acceptable GPS coordinate locations; wherein the electronic device non-transitory memory is programmed to: determine if the current location of the animal is approaching the one or more perimeter boundaries, outside of the one or more perimeter boundaries, within a predetermined distance of the one or more perimeter boundaries, or at the one or more perimeter boundaries; and electronically prodding the animal, using the electronic device, based on the determination.

18 Claims, 5 Drawing Sheets

(56) References Cited

U.S. PATENT DOCUMENTS

| | | | | |
|---|---|---|---|---|
| 5,322,034 A * | 6/1994 | Willham | ............... | A01K 11/006 119/174 |
| 5,868,100 A * | 2/1999 | Marsh | ................... | A01K 15/023 119/421 |
| 5,901,660 A * | 5/1999 | Stein | .................... | A01K 11/006 119/174 |
| 6,232,880 B1 * | 5/2001 | Anderson | ............ | A01K 15/023 119/421 |
| 6,581,546 B1 * | 6/2003 | Dalland | ............... | A01K 15/023 119/712 |
| 6,591,786 B1 * | 7/2003 | Davis | .................... | A01K 11/00 119/719 |
| 6,901,369 B2 * | 5/2005 | Cureton | .................. | A01K 5/02 705/1.1 |
| 7,173,535 B2 * | 2/2007 | Bach | .................... | A01K 15/023 119/712 |
| 7,681,527 B2 * | 3/2010 | Pratt | ...................... | A01K 29/00 119/174 |
| 7,753,007 B1 * | 7/2010 | Anderson | ............ | A01K 15/028 119/721 |
| 8,736,440 B2 * | 5/2014 | Kwak | ................... | A01K 11/006 119/51.02 |
| 8,851,019 B2 * | 10/2014 | Jesurum | ............... | A01K 15/023 119/721 |
| 9,007,218 B2 * | 4/2015 | Chamberlain | ....... | A01K 11/006 119/712 |
| 2008/0168953 A1 * | 7/2008 | Kurt | .................... | A01K 15/021 119/859 |
| 2012/0204811 A1 * | 8/2012 | Ryan | .................... | A01K 15/021 119/720 |

* cited by examiner

SYSTEM AND METHOD FOR ANIMAL CORRALLING AND TRACKING

BACKGROUND

Field of the Invention

The present inventions relate to the device conceived and the method utilized to track, monitor, and electronically corral host animals (such as wildlife herds and livestock/cattle).

SUMMARY

A method of animal corralling and tracking includes: implanting an electronic device within an animal, the electronic device comprising one or more processors with non-transitory memory; receiving, with the electronic device, a GPS (global positioning satellite) signal defining a current location of the animal; selecting, on a digital map, acceptable GPS coordinate locations forming one or more geographic regions with one or more perimeter boundaries; wirelessly programming the electronic device with the selected acceptable GPS coordinate locations; wherein the electronic device non-transitory memory is programmed to: determine if the current location of the animal is approaching the one or more perimeter boundaries, outside of the one or more perimeter boundaries, within a predetermined distance of the one or more perimeter boundaries, or at the one or more perimeter boundaries; and electronically prodding the animal, using the electronic device, based on the determination.

The electronic device may be implanted within a head or neck of the animal. The electronic device may further include an electromagnetic generator. The electromagnetic generator may produce electricity as the animal moves its head or neck. The selecting on a digital map may include using a touch screen to select one or more of the acceptable GPS coordinate locations. The one or more geographic regions may further comprise a selected time-of-day, season-of-the-year, and/or calendar date associated with a specific region of the one or more geographic regions. The specific region includes a feeding location, a shelter location, a grazing location, an animal maintenance location, or a corralling location. The wirelessly programming of the electronic device may take place after the electronic device is implanted. The wirelessly programming of the electronic device may take place before the electronic device is implanted. The specific region may include a wireless transceiver that performs the wireless programming or updates to the wireless programming of the electronic device. The wireless transceiver may be a Near Field Communications (NFC) device. The NFC device may receive the wireless programming or updates to the wireless programming as the animal is feeding in a predetermined location. The NFC device may transmit the animal's hormone levels, temperatures, historical temperatures, historical hormone levels, historical location history, or a combination thereof. The method may further comprise: waking one or more program systems of the electronic device on a schedule. The one or more program systems may include a biometric measurement system, a prodding system, or a location system. The biometric system may include one or more hormone measurement sensors, one or more temperature sensors, one or more pulse sensors, or one or more respiration sensors. The prodding system may include one or more acoustic transducers, electronic shock devices, and/or tactile devices. The non-transitory memory may be long term flash memory. The electromagnetic generator may be a kinetic generator. The method may further comprise notifying an animal owner of a status of the animal based on predetermined events.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

It will be readily understood that the components of the present invention, as generally described and illustrated in the Figures herein, may be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings.

Figure 1:
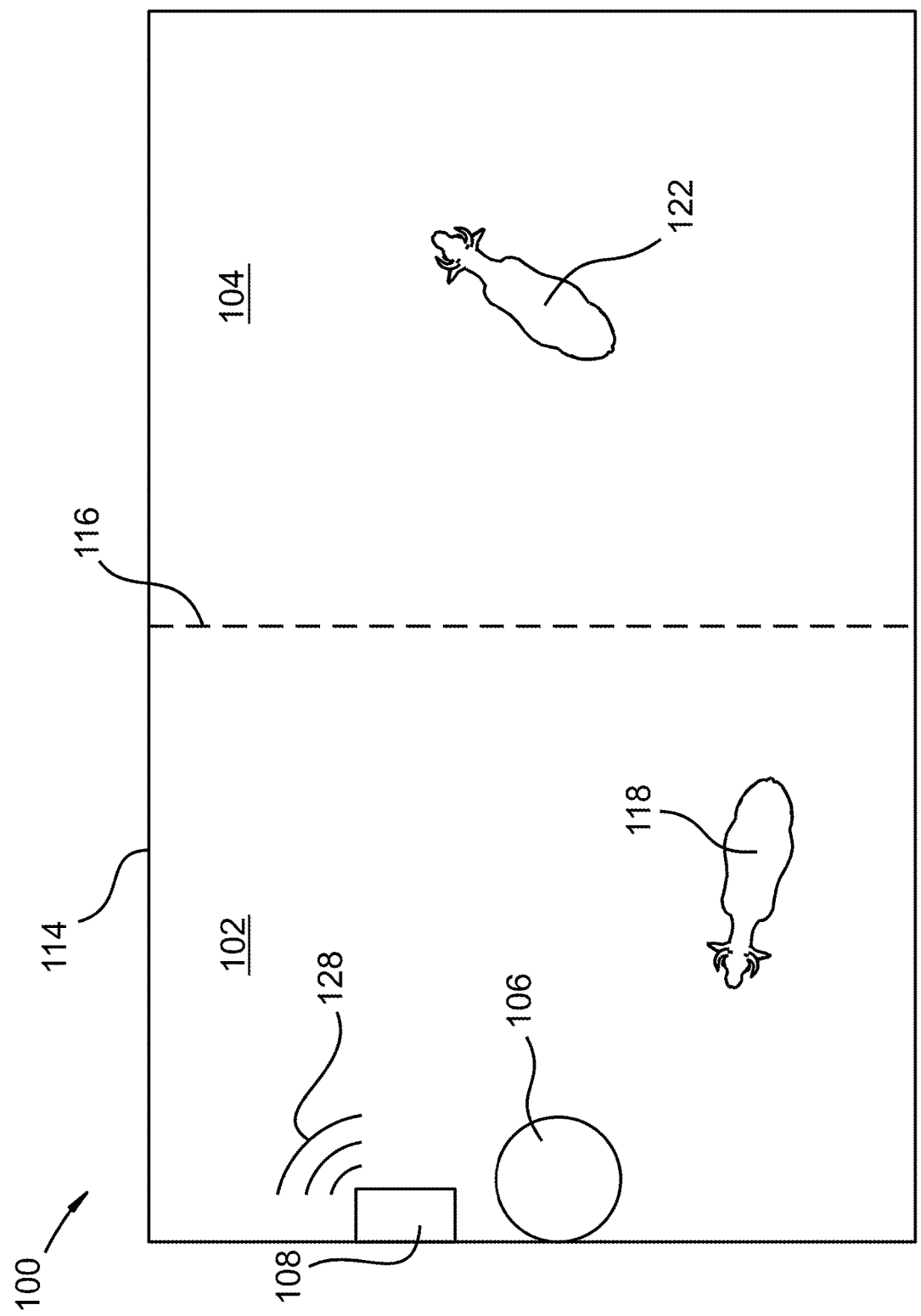
FIG. 1 shows a digital fence map in accordance with an embodiment of the invention.

FIG. 1 shows a digital fence map 100 including virtually fenced geographic regions 102/104, perimeter boundaries 114/116, predefined feeding area 106, fixed communications device 108, wireless signal 128, and animals 118/122. Geographic regions 102/104 may be selected on a digital map such as Google maps, MapQuest, Google Earth, or any other digital map relating GPS coordinate locations to a physical geographic region. Geographic regions 102/104 represent physical locations such as a pasture, grazing field, yard, or lot. A user of the virtual fencing system described herein is able to open a digital map and select a geographic region of the map creating a virtual fence 114/116 (perimeter boundaries of regions 102/104). The geographic fencing regions may be selected by a user freeform drawing over a digital map or by selecting corners, radii, lines, intersections, or areas representing geographic regions of earth. A touch screen or mouse selection may be used to assist a user in defining geographic boundaries or geographic boundary overlays. When a geographic region is selected, perimeter boundaries and areas within the perimeter boundaries may be defined using known GPS (global positioning satellite) coordinate data. The GPS coordinate data defining the selected geographic regions and boundaries may then uploaded into an implantable or implanted electronic animal prodding device. Animals 118/122 have electronic prodding devices (See FIG. 4) implanted within the body of the animal. The GPS coordinate data may be uploaded before implantation or loaded or updated after implantation within animals 118/122. Each animal may have a unique GPS coordinate locations based on a desired range or position on the animals. For instance, animal 118 may be kept within area 102 while animal 122 may be kept within area 104. Areas may be dynamically set based on dates, time of day, time of year, season, etc. One electronic prodding device may have a library of GPS location data and be sorted and used based on programming within a memory of the prodding device. For example, a cow with a show of fertility may be automatically prodded to an area where a bull is stationed. Fertility data along with other biometric data may be collected by the implanted device and used to dynamically change a GPS boundary of the animal. Other features and functionality is described further in relation to FIGS. 2-5. As animal 118/122 approaches perimeter boundary 116/114, a location based wake signal may be sent to wake up a notification system within the device. A notice may then be given to warn animal 118/122 of an approaching boundary. If the animal heeds the notice (vibration, sound, slight shock) and stops progressing toward perimeter 114/116, the implanted electronic device may go back to sleep and wait for a location based wake signal to be generated. If the animal continues to progress toward the perimeter or crosses the perimeter a strong shock, vibration, and/or sound may be given to animal 118/122.

Figure 2:
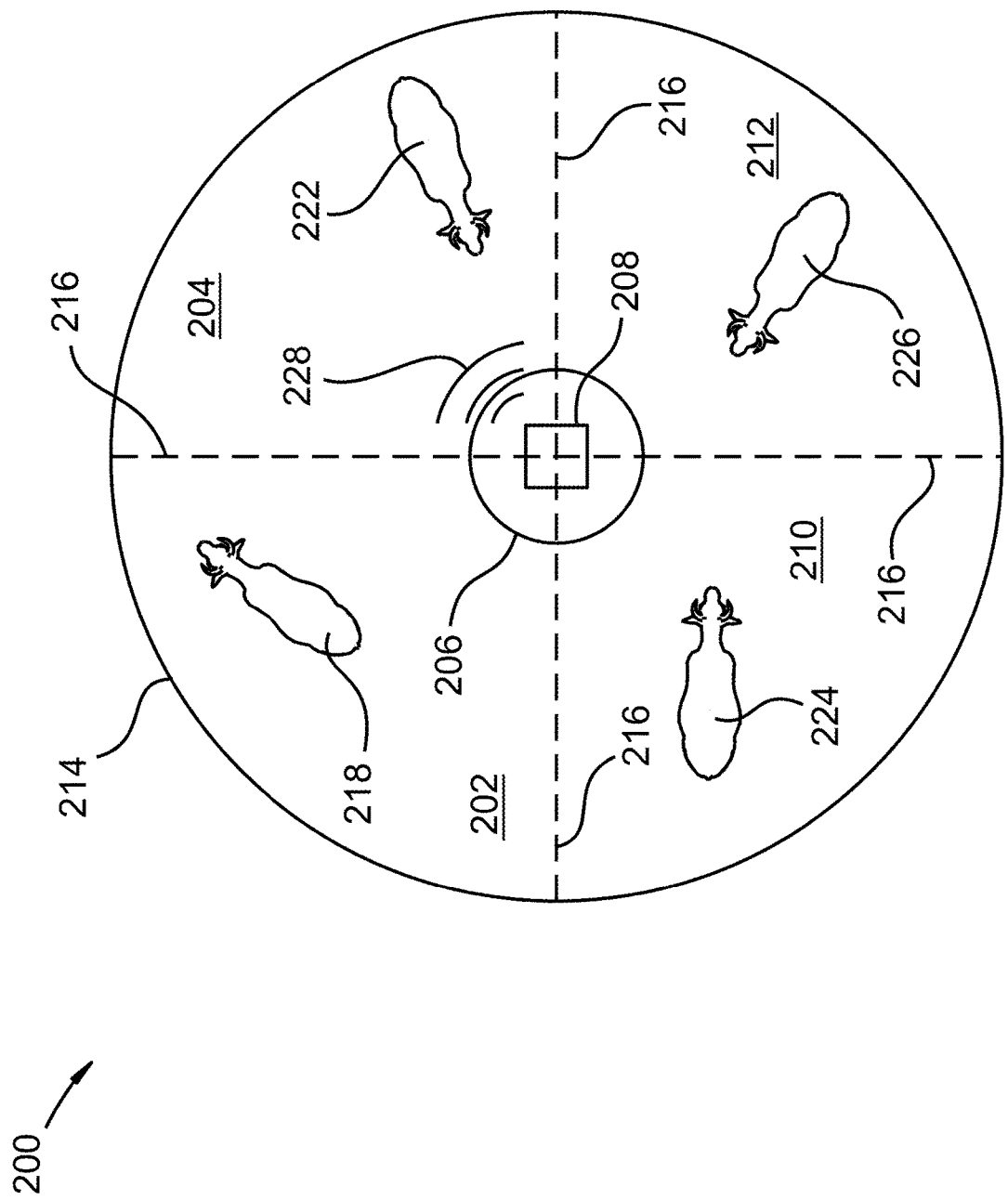
FIG. 2 shows a digital fence map in accordance with an embodiment of the invention.

FIG. 2 shows a digital fence map 200 including virtually fenced geographic regions 202/204/210/212, perimeter boundaries 214/216, predefined feeding area 206, fixed communications device 208, wireless signal 228, and animals 218/222/224/226. Geographic regions 202/204 may be selected on a digital map such as Google maps, MapQuest, Google Earth, or any other digital map relating GPS coordinate locations to a physical geographic region. Geographic regions 202/204 represent physical locations such as a pasture, grazing field, yard, or lot. A user of the virtual fencing system described herein is able to open a digital map and select a geographic region of the map creating a virtual fence 214/216 (perimeter boundaries of regions 202/204/210/212). The geographic fencing regions may be selected by a user freeform drawing over a digital map or by selecting corners, radii, lines, intersections, or areas representing geographic regions of earth. A touch screen or mouse selection may be used to assist a user in defining geographic boundaries or geographic boundary overlays. When a geographic region is selected, perimeter boundaries and areas within the perimeter boundaries may be defined using known GPS (global positioning satellite) coordinate data. The GPS coordinate data defining the selected geographic regions and boundaries may then uploaded into an implantable or implanted electronic animal prodding device. Animals 218/222/224/226 have electronic prodding devices (See FIG. 4) implanted within the body of the animal. The GPS coordinate data may be uploaded before implantation or loaded or updated after implantation within animals 218/222/224/226. Each animal may have a unique GPS coordinate locations based on a desired range or position on the animals. For instance, animal 218 may be kept within area 202 while animal 222 may be kept within area 204. Areas may be dynamically set based on dates, time of day, time of year, season, etc. One electronic prodding device may have a library of GPS location data and be sorted and used based on programming within a memory of the prodding device. For example, a cow with a show of fertility may automatically prodded to an area where a bull is stationed. Fertility data along with other biometric data may be collected by the implanted device and used to dynamically change a GPS boundary of the animal. Other features and functionality is described further in relation to FIGS. 2-5. As animal 218/222/2224/226 approaches perimeter boundary 216/214, a location based wake signal may be sent to wake up a notification system within the device. A notice may then be given to warn the animal(s) of an approaching boundary. If the animal heeds the notice (vibration, sound, slight shock) and stops progressing toward perimeter 214/216, the implanted electronic device may go back to sleep and wait for a location based wake signal to be generated. If the animal continues to progress toward the perimeter or crosses the perimeter a strong shock, vibration, and/or sound may be given to the animal(s).

Figure 3:
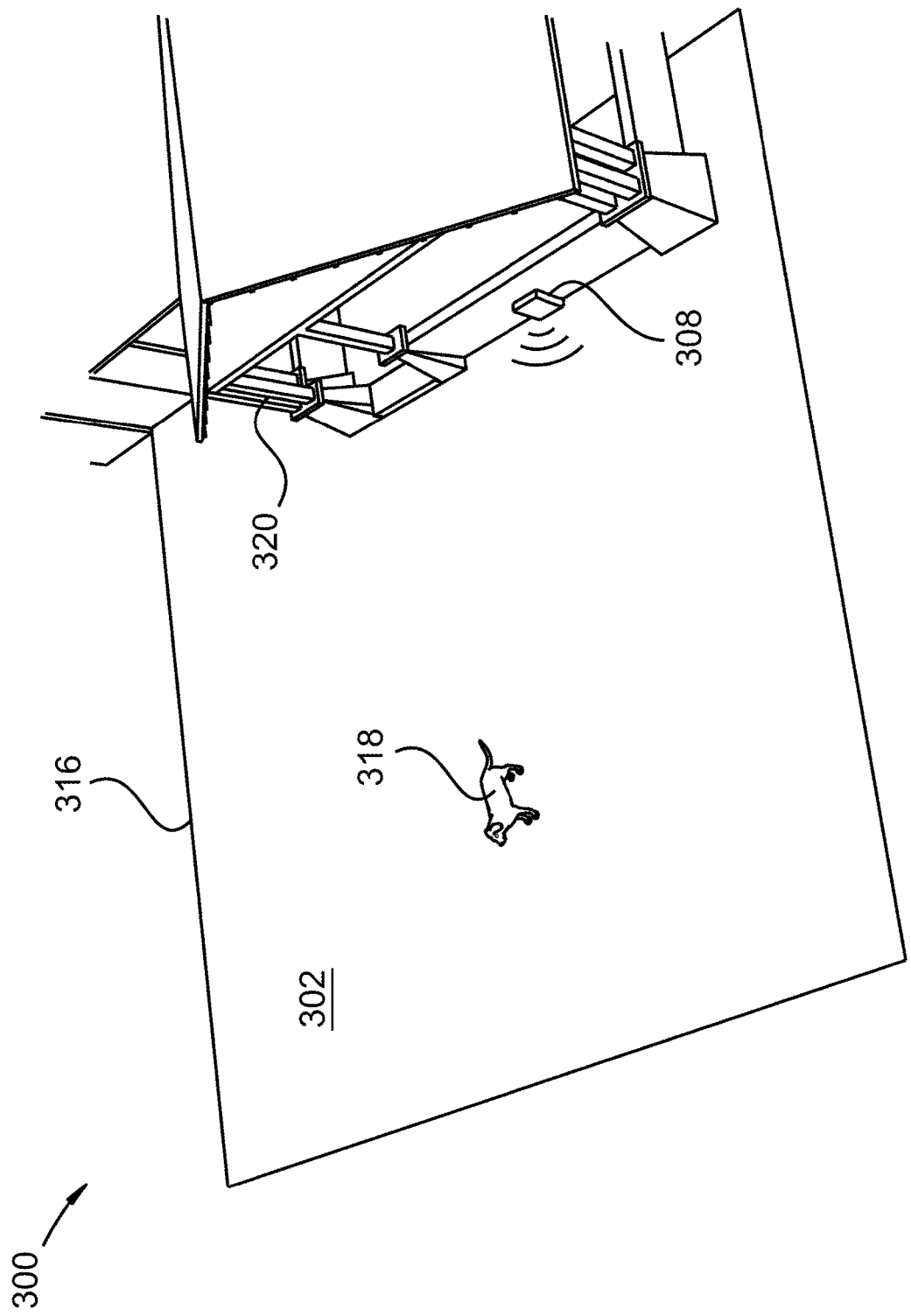
FIG. 3 shows a digital fence map in accordance with an embodiment of the invention.

FIG. 3 shows a digital map 300 of a house 320, a yard area 302, perimeter boundaries 316, wireless transmitter 308, and dog with an implanted device 318. A home owner selected area 302 for a virtually defined yard for dog 318. The GPS related location data of the virtually defined yard was uploaded into a prodding device implanted within dog 318. As dog 318 approached perimeter boundary 316, a location based wake signal may be sent to wake up a notification system within the device. A notice may then be given to warn dog 318 of an approaching boundary. If the dog heeds the notice (vibration, sound, slight shock) and stops progressing toward perimeter 316, the implanted electronic device may go back to sleep and wait for a location based wake signal to be generated. If the dog continues to progress toward the perimeter or crosses the perimeter a strong shock, vibration, and/or sound may be given to dog 318.

Figure 4:
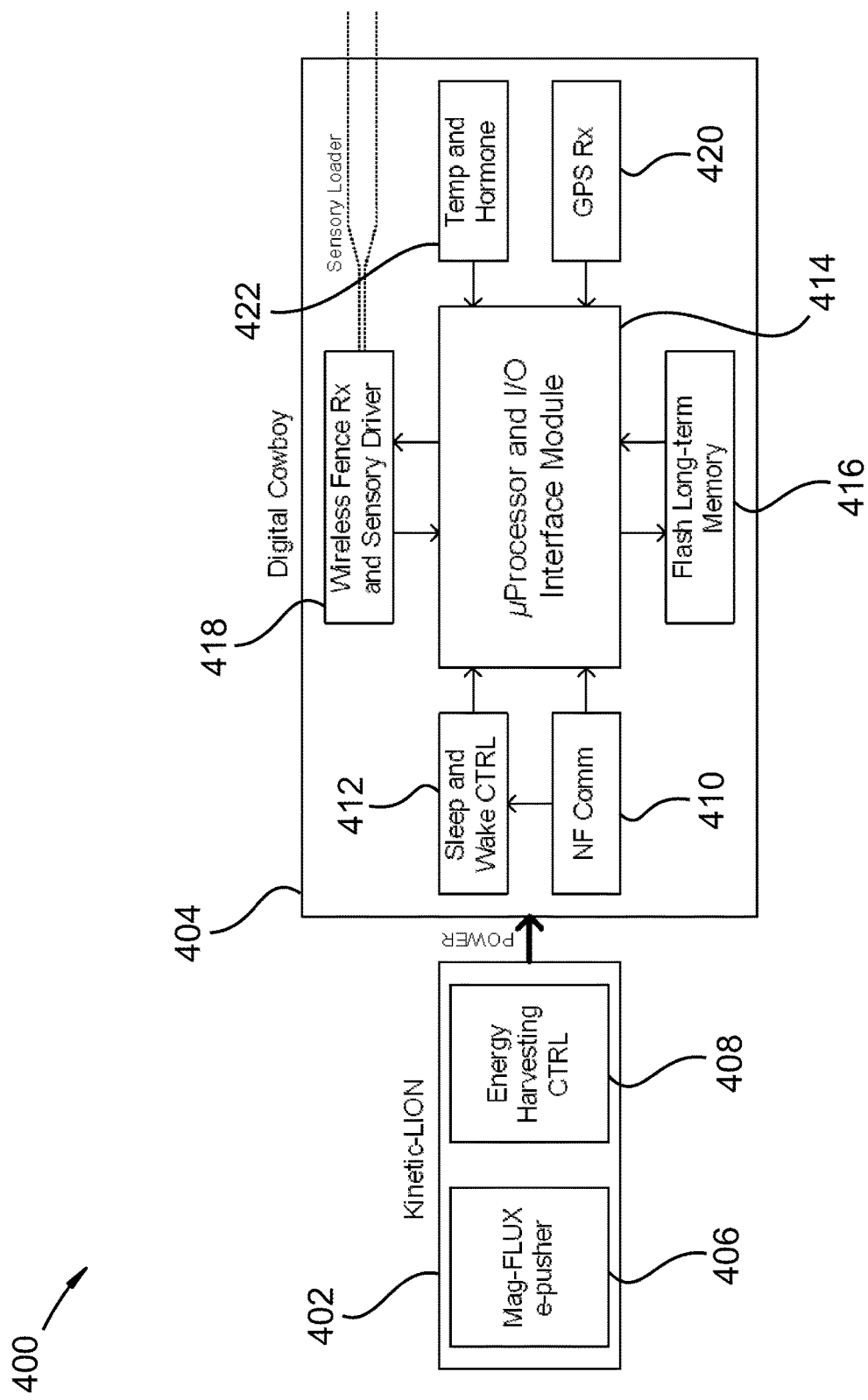
FIG. 4 shows a functional block diagram in accordance with an embodiment of the invention.

FIG. 4 shows function block diagram 400 of an implantable circuit of the present invention. The implantable circuit includes a electromagnetic generator 402 and a main circuit 404.

The implantable circuit device 400 and method disclosed herein is used for electronically setting a grazing perimeter, corralling animals, tracking and monitoring animals over extended spans of time. The device and method disclosed herein includes: a micro-processor board 404 used to control a scheduled menu of operations to execute before returning to a super-deep sleep mode 412. During the super-sleep mode 412, only isolated battery charging circuitry operates to trickle-charge the primary battery.

The system is triggered into wake mode 412 by the Near-field Communication (NFC) function 410, wherein an altogether new schedule of operations is executed before interacting with the NFC commands to determine if it should return to deep-sleep mode 412. Particularly, the NFC sets a new wake pattern if the host animal need be electronically corralled. During electronic corralling, the wake time duty cycle and frequency is such that the host animal can be prodded electronically several times a second, as needed.

When the system awakes, it also quickly executes several scheduled operations including, measuring host temperature, pulse, and (several) hormone levels 422, determining GPS coordinates 420, measuring battery quality and charge level 414. Finally, these values are written to long term flash memory 416. The subsequent wake-cycle schedule may be adapted if the current cycle data indicated.

Accordingly, it is a general operational goal and purpose of the present invention to provide a suitable device, and a method (software executable program) to electronically set a grazing perimeter, electronically corral, track, monitor a host entity over an extended period of time (assumed to be the entire life of the host).

In order to attain the desired objective, the device utilizes sub-modules that can be placed into deep sleep modes wherein power usage is negligible. Necessarily, these devices are awakened in exceedingly short periods of time, wherein they execute their prescribes duties, and are returned to deep-sleep modes. The complimentary power-module provides high-power availability for the short durations required, followed by lengthy and slow energy harvesting and charging periods.

For example a wireless grazing perimeter can be assigned in a graze able area, electronically corralling host animals (which technology is acoustic-electric versus simply electric) and reporting the GPS coordinates of an out-of-boundary animal. An implanted host may errantly wander, or be taken without permission, out of a prescribed geographical boundary. While wandering, the host is acoustically prodded to return to within the wireless fence, which prodding-intensity increases as the perimeter is further violated. If the boundary is significantly exceeded and the GPS coordinates indicate an extreme out-of-bounds condition, prodding is halted and the subscriber would be wirelessly notified (as described previously).

Another example, would be that a host animal may be periodically monitored until a certain set of criteria are met, as determined by measurement data from the host, which would indicate pregnancy, or gestation cycle fertility. This data set would cause the system to discontinue the standard wake/deep-sleep cycle until sufficient energy was stored to transmit a message wirelessly to a centrally networked data-base, wherein the data-base program would send the host animals GPS coordinates and gestation state data to the subscriber.

A device capable of tracking, monitoring, and electronically corralling a host is presented in the following figures, and the method of controlling the schedule and menu of functions executed by each is presented. The invention includes as part of the new art, the order of sleep/wake cycles, and the manner and method by which wake cycles are triggered.

The first sub-module is the "Sleep and Wake CTRL" (412). This module controls when any battery power may begin to be used by any other function of the Digital Cowboy, but not when it ends power usage; consequently, all modules remain in deep-sleep mode until sufficient power is provided to that module, with a subsequent ENABLE signal, both power and enable provided from 412. The Sleep and Wake module may be prohibited from its pre-determined program by a low-power signal from the Power-source 402.

The NF communications module 410 may send a wake signal to the above Sleep and Wake CTRL module 412 when it is energized externally through RF power in the power-band, and the proper identification code is provided and verified by the NF Communication module 410. Note that the NF Communication module is not battery powered when externally excited, and will only send a "wake" interrupt when a proper identification code is provided. When the system has been properly awoken, the NF Communication module may be, and generally will be, powered by the dedicated battery within module 402.

The data from "Flash Long-term Memory" 416 is relayed to local temporary storage devices or networked wireless systems for eventual data-center storage. The NF Communication 410 module is the dedicated path to offload and upload data and field program updates. Modifications to the schedule of functions to be executed on the next wake cycle are stored to Flash 416 in the PRGM memory space before returning to deep sleep mode. While awake, and according to schedule or NFC 410 interrupted commands, the "host data" stored in long term memory 416 may be polled and streamed via the NFC module for relay to remote data-storage centers and subject to additional processing and manipulations. The relayed wireless devices are many: including satellite phone, cellular, or WiFi networks.

The Electric or wireless fence function is hosted on the "Wireless Fence Rx and Sensory Driver" module 418, which determines relative position via differential remote locating. The position is reported to the processor 414 and feedback commands are returned. The feedback commands generate acoustic prompts that encourage an animal to return toward a boundary, or not approach that boundary. The acoustic prompts can be exaggerated to uncomfortable electrical prodding when necessary.

The GPS coordinates 420 are read, processed, and stored according to the program schedule. The GPS module 420 is a receive only module that reports its determined coordinates upon being enabled and returns immediately to deep-sleep mode. The coordinates are compared to a pre-determined boundary (i.e. grazing area), and if determined to be within the boundary, the coordinates are stored to long term Flash 416; otherwise, if outside of the boundary, additional program steps are taken (i.e. notify subscriber and update remote storage server via wireless data ping).

The "Temp and Hormone" 422 module converts various analog sensor signals into discrete measurement via a multiplexed analog-to-digital converter (ADC), and passes on those discrete values to the processor 414 for further processing and long term storage.

Figure 5:
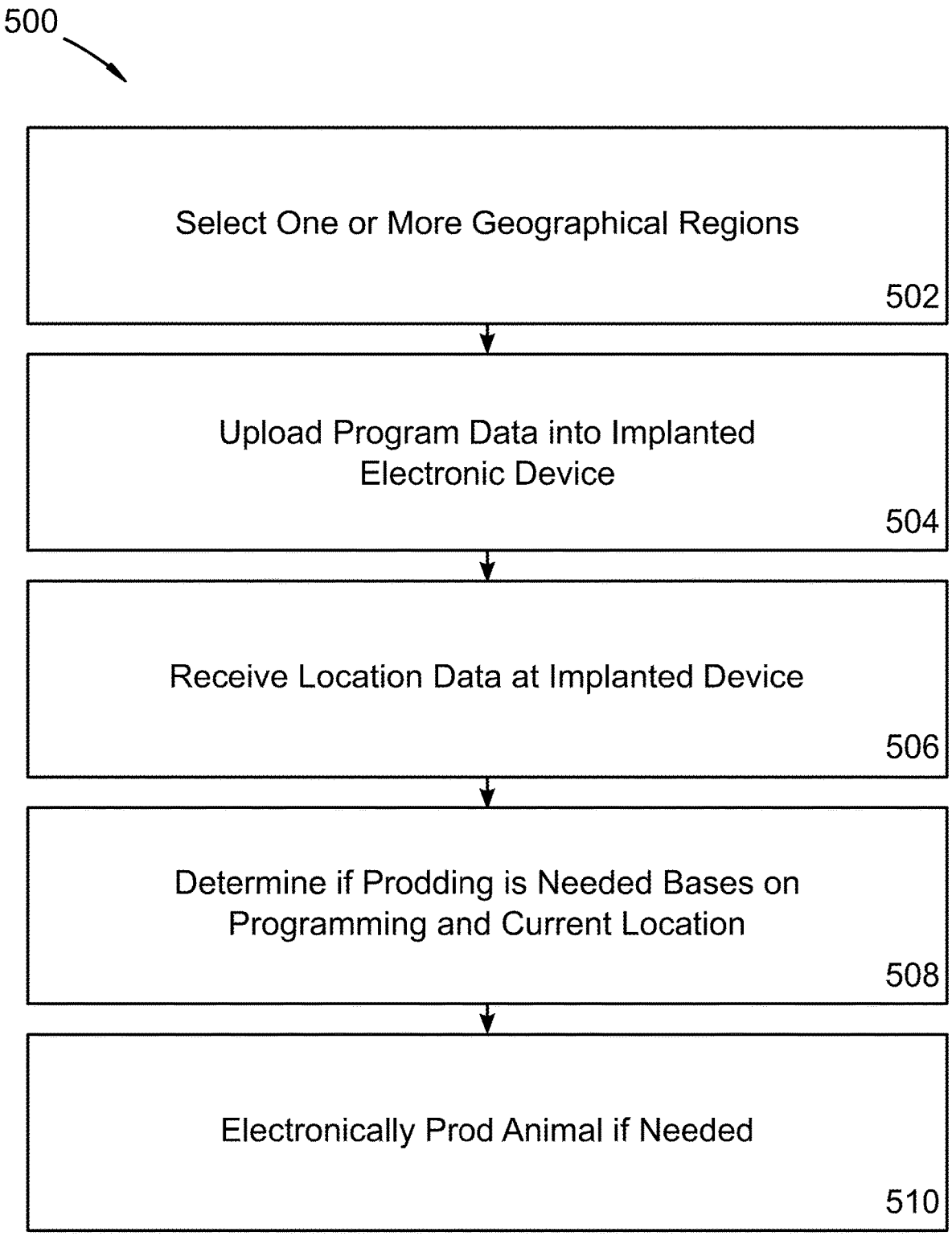
FIG. 5 shows a flow diagram in accordance with an embodiment of the invention.

FIG. 5 shows a function block diagram 500 in accordance with an embodiment of the invention. In this embodiment, a user selects one or more geographical regions 502 in building a virtual fencing system. The GPS data is then uploaded 504 to the electronic prodding device. The uploading 504 may take place using a NFC device or other wireless device such as Bluetooth or Wi-Fi. The NFC device may be connected to a feeding device of the animal. The NFC device may also include a solar power system allowing for remote placement. The NFC device may also be network connected by cellular data, GSM, Wi-Fi, or a wired connection. The NFC device may be connected to a database server and obtain information from a cloud based mapping program such as Google maps or map Quest. Once the device is loaded with GPS data and implanted within an animal, the electronic device starts receiving GPS location data 506. Program code within the device then is able to determine if prodding is needed based on the programming and a Current GPS location 508. Then the animal is prodded as needed 510. The prodding may be graduated such that the animal receives a stronger or louder prodding as it get closer to a defined perimeter.

The apparatus and methods disclosed herein may be embodied in other specific forms without departing from their spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

The invention claimed is:
1. A method of animal corralling and tracking comprising:
   implanting an electronic device within an animal, the electronic device comprising one or more processors with non-transitory memory and a kinematic generator;
   receiving, with the electronic device, a GPS (global positioning satellite) signal defining a current location of the animal;

selecting, on a digital map, acceptable GPS coordinate locations forming one or more geographic regions with one or more perimeter boundaries;

wirelessly programming the electronic device with the selected acceptable GPS coordinate locations;

wherein the electronic device non-transitory memory is programmed to: determine if the current location of the animal is approaching the one or more perimeter boundaries, outside of the one or more perimeter boundaries, within a predetermined distance of the one or more perimeter boundaries, or at the one or more perimeter boundaries; and electronically prodding the animal, using the electronic device, based on the determination.

2. The method of claim 1, wherein the electronic device is implanted within a head or ear of the animal.

3. The method of claim 2, wherein the kinematic generator produces electricity as the animal moves its head.

4. The method of claim 1, wherein the selecting on a digital map includes using a touch screen to select one or more of the acceptable GPS coordinate locations.

5. The method of claim 1, wherein the one or more geographic regions further comprise a selected time-of-day, season-of-the-year, and/or calendar date associated with a specific region of the one or more geographic regions.

6. The method of claim 5, wherein the specific region includes a feeding location, a shelter location, a grazing location, an animal maintenance location, or a corralling location.

7. The method of claim 6, wherein the specific region includes a wireless transceiver that performs the wireless programming or updates to the wireless programming of the electronic device.

8. The method of claim 7, wherein the NFC device transmits the animal's hormone levels, temperatures, historical temperatures, historical hormone levels, historical location history, or a combination thereof.

9. The method of claim 6, wherein the wireless transceiver is a Near Field Communications (NFC) device.

10. The method of claim 9, wherein the NFC device receives the wireless programming or updates to the wireless programming as the animal is feeding in a predetermined location.

11. The method of claim 1, wherein the wirelessly programming of the electronic device takes place after the electronic device is implanted.

12. The method of claim 1, wherein the wirelessly programming of the electronic device takes place before the electronic device is implanted.

13. The method of claim 1 further comprising: waking one or more program systems of the electronic device on a schedule.

14. The method of claim 13, wherein the one or more program systems include a biometric measurement system, a prodding system, and a location system.

15. The method of claim 14, wherein the biometric system includes one or more hormone measurement sensors, one or more temperature sensors, one or more pulse sensors, or one or more respiration sensors.

16. The method of claim 1, wherein the prodding system includes one or more acoustic transducers, electronic shock devices, and/or tactile devices.

17. The method of claim 1, wherein the non-transitory memory is long term flash memory.

18. The method of claim 1 further comprising: notifying an animal owner of a status of the animal based on predetermined events.

* * * * *